United States Patent [19]

Lawrie et al.

[11] Patent Number: 4,702,112

[45] Date of Patent: Oct. 27, 1987

[54] ULTRASONIC PHASE REFLECTOSCOPE

[75] Inventors: William E. Lawrie; Thomas Powers, Jr., both of Lynchburg, Va.; Joseph W. Brophy, Redmond, Wash.

[73] Assignee: The Babcock & Wilcox Company, New Orleans, La.

[21] Appl. No.: 764,912

[22] Filed: Aug. 12, 1985

[51] Int. Cl.⁴ ............................................. G01N 29/04
[52] U.S. Cl. ........................................ 73/629; 73/606; 73/624
[58] Field of Search .......................... 73/629, 606, 624; 367/102, 113

[56] References Cited

U.S. PATENT DOCUMENTS

| 3,836,952 | 9/1974 | Johnson | 367/48 |
| 4,155,258 | 5/1979 | Engeler et al. | 73/626 |
| 4,598,589 | 7/1986 | Riley | 128/660 |

OTHER PUBLICATIONS

"Encyclopedia on Cathode-Ray Oscilloscopes and Their Uses", Rider et al, John F. Rider Publishing, Inc., 1959, Second Edition, pp. 14-1 to 14-7.

Primary Examiner—Howard A. Birmiel
Attorney, Agent, or Firm—Vytas R. Matas; Robert J. Edwards

[57] ABSTRACT

An ultrasonic apparatus and method for testing a material comprises an oscillator which generates a selected frequency in the ultrasonic range. A transducer is connected to the oscillator for applying an ultrasonic signal to the material and for receiving an echo signal back from the material. Two phase detectors are utilized one of which receives the echo signal and an in-phase oscillator signal to generate a first display signal, and the other of which receives a quadrature signal which is 90° out of phase from the oscillator signal, as well as the echo signal to generate a second display signal. The first and second display signals are utilized in a visual display such as a cathode ray tube, to generate an image. The image changes according to the phase shift between the ultrasonic signal transmitted into the material and the echo signal, which, in turn, can be utilized to determine the presence and depth of a flaw or boundary in the material.

13 Claims, 2 Drawing Figures

ULTRASONIC PHASE REFLECTOSCOPE

FIELD AND BACKGROUND OF THE INVENTION

The present invention relates, in general, to non-destructive ultrasonic testing and, in particular, to a new and useful apparatus and method for detecting the size, depth, orientation and location of flaws in material by sensing the change in phase of an ultrasonic echo pulse.

Conventional ultrasonic testing provides time, amplitude and spatial information that is combined through mechanical and electrical apparatus to form A, B and C scans for flaw detection and sizing. The most commonly used technique is time-amplitude or A scan ultrasonic testing. All of these techniques make use of either a continuous wave or a pulse excitation and time reference signal. The primary limitation of these techniques are that they only allow discrimination via signal amplitudes, time separation or spatial separation. These parameters are insufficient to independently define the size, depth, orientation and location of a flaw.

In coarse-grained materials, ultrasonic energy which is backscattered at grain boundaries, provides a signal which is continuous during the time that pulse echoes are being received. These backscattered signals may totally obscure the echoes. Evidence shows that if a defect is present to reflect the ultrasonic energy, the phase of the composite echo may be used to indicate the presence of the defect even though a distinctive pulse may not appear above the noise. The noise is commonly referred to as "grass". Unfortunately, as the transducer used to generate and receive the ultrasound is scanned over the surface, the amplitude will reach a single or at most several peaks before decaying. In contrast, phase would continuously change in one direction with transducer motion, stop when the transducer is at the point of closest approach, and reverse. A single phase measurement is not sufficient. What is needed is a device to sense the change in phase with transducer position. Also, it must indicate the difference between random phase variations obtained with only grain boundary reflections, and a distinctive pattern obtained with a reflector such as a flow.

U.S. Pat. No. 4,253,337 to Vasile discloses an ultrasonic testing method which utilizes phase measurements and/or phase shifting of ultrasonic materials. Vasile discloses a method of evaluating a defect or discontinuity in an object. As such the reference utilizes the transmission of an ultrasonic wave into the object and the detection of the wave after it has propagated through the discontinuity. The depth of the discontinuity is also considered with respect to the change in phase and amplitude of the detected wave which are compared to values of a wave propagating in the absence of a discontinuity. Vasile does not however detect the change in phase of the echo pulse with transducer position and does not use two phase detectors utilizing in-phase and quadrature reference signals. In addition, a rotating vector display is not utilized which is used in the present invention as will be explained fully hereinunder.

U.S. Pat. No. 4,003,244 to O'Brien et al discloses an ultrasonic pulse echo thickness apparatus wherein the search signal and the echo signal are amplified so as to be in equal magnitude and are also phase shifted so as to be in phase with each other. In this manner, overall system accuracy is increased. Thus, this reference deals with the phase of the signal, however, it does not teach the sensing of a change in phase of an echo pulse with transducer position. O'Brien also does not utilize other features of the present invention.

SUMMARY OF THE INVENTION

The present invention is drawn to an apparatus and method of detecting the size, depth, orientation and location of flaws in materials. The invention can be utilized even with coarse-grained materials which suffer from backscattered noise.

According to the invention, a change in phase of an echoed pulse with transducer position is sensed. Two phase detectors are used, one using an in-phase reference signal and the other using a quadrature reference signal. These two phase detectors permit the generation of a rotating vector display on a cathode ray tube. In this manner the pattern of phase change can be monitored to detect a discontinuity and to determine the depth and location of the discontinuity in the material. Discontinuities may be either discrete defects or intended material variations which influences elastic wave velocities.

The present invention is a specific application of a more general concept.

The phase of an echo relative to the phase of the original pulse is given by the relationship:

$$\phi = 2kR - \sigma$$

Wherein:
$\phi$ = detected phase magnitude;
$k = (2\pi/\text{wavelength of pulse})$;
$R$ = distance from transducer to reflector (flaw); and
$\sigma$ = phase shift during reflection ($\pi$ at a reflection from a lower impedance).

The phase is thus a monotonic function of R.

The present invention utilizes a combination of a distinctive phase shift pattern, obtained on a vectorscope, through the use of two phase detectors, using in-phase and quadrature (90° out of phase) reference signals. The use of two phase detectors is necessary to generate a rotating vector display on a cathode ray tube of the vectorsope. According to the invention, a pattern of phase change rather than a random phase change is used to indicate the presence of a defect.

Alternative techniques which determine the relationship between the phase detected signal, excitation frequency and reflector position are possible. Unique relationships between the detected phase, excitation frequency and reflector position can be established by suitable calibration from standard test blocks.

The relationship between frequency, phase and distance can be written as:

$$\left.\frac{d\phi}{df}\right|_R \cdot \left.\frac{df}{dR}\right|_\phi \cdot \left.\frac{dR}{d\phi}\right|_f = -1$$

This relationship is known as the cycle chain rule and is a consequence of the detected phase being a function of frequency and distance between the transducer and reflector.

$$\phi = F(f, R)$$

where f is frequency and R is distance.

The factor $$\left.\frac{d\phi}{df}\right|_R$$

can be determined by varying the excitation frequency f while the transducer is at a fixed position. As f is varied, the phase of the echo will change as indicated by the output of the phase detector which oscillates between maxima and minima. The phase goes through one cycle when the frequency changes by Δf where:

$$\Delta F = \frac{C}{2R}$$

where C is the velocity of sound in the test material.

This provides a depth measurement, equivalent to measuring time t, through $$R = C/2 \, \Delta f$$

The orientation of planar reflectors relative to the axis of the transducer beam can be determined. As the transducer continuously scans over the surface in one direction, the phase of the reflected signal will change first in one direction, stop and then change in the opposite direction. The transducer position at which the rate of phase change is zero is the point of closest approach. This point of closest approach of the transducer to the defect may not be the point at which maximum amplitude is obtained. The difference in positions of zero rate of change of phase and maximum amplitude is dependent upon the direction of the ultrasonic beam axis and upon the orientation of the reflecting surface. This is also true for edge diffracted or mode converted waves.

Accordingly, an object of the present invention is to provide an ultrasonic apparatus and method for testing a material which comprises or utilizes an oscillator for generating an oscillator signal at a a selected frequency in the ultrasonic range, transducer means connected to the oscillator for applying an ultrasonic signal to the material and for receiving an echo signal back from the material, phase detector mixing means connected to the transducer means and to the oscillator for mixing the echo signal with an in-phase oscillator signal to produce a first display generating signal, and with a quadrature oscillator signal which is out of phase from the in-phase signal by 90°, to produce a second display generating signal, and display means connected to said phase detector mixing means for producing a visual image from the first and second display generating signals which is representative of the degree of phase shift between the ultrasonic signal supplied into the material and the echo signal which in turn can be used to determine the presence and depth of a flaw or boundary in the material.

A further object of the invention is to provide an ultrasonic apparatus which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
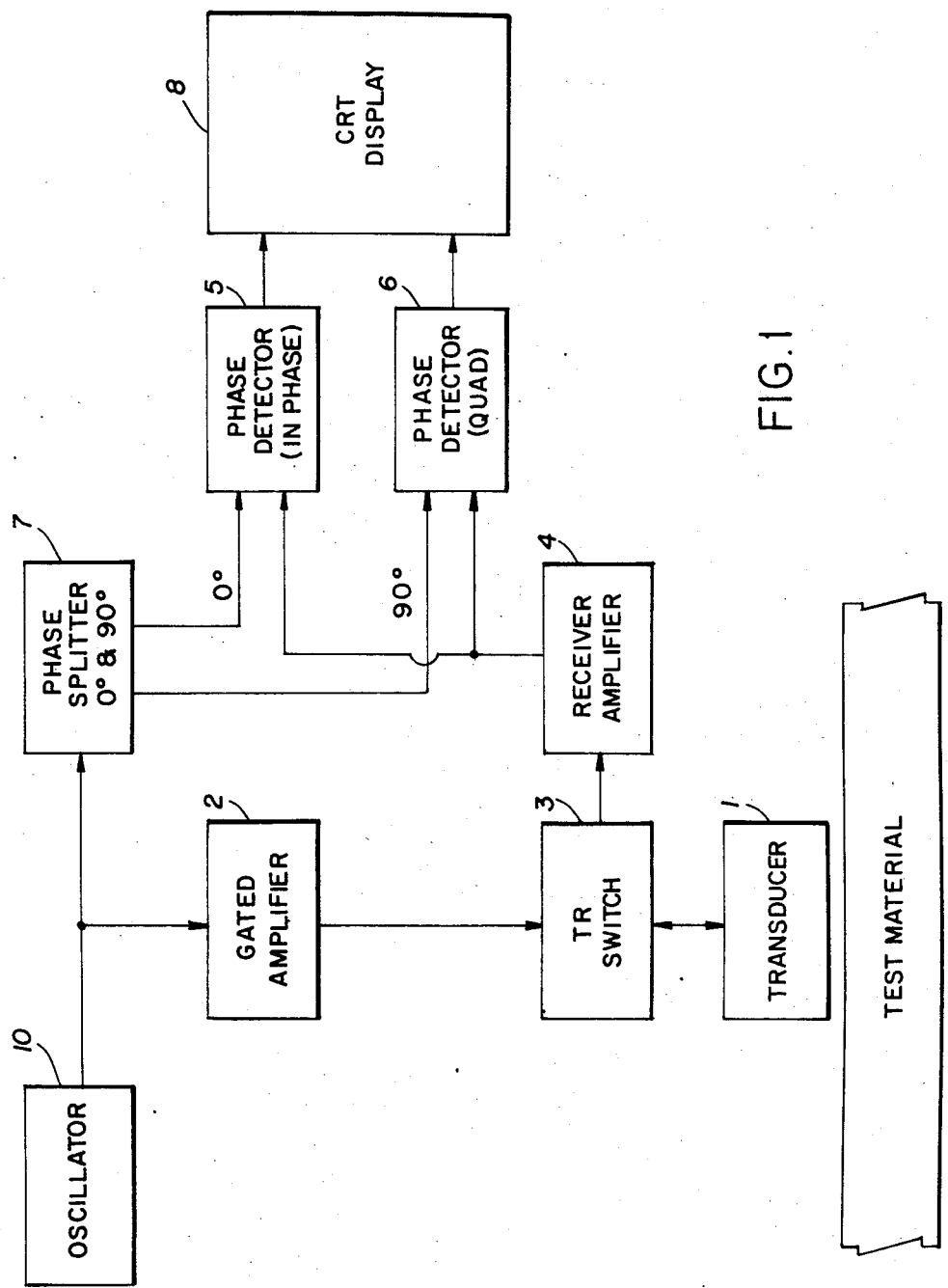
FIG. 1 is a block diagram for one type of phase sensitive ultrasonic instrument according to the invention.

Referring to the drawings, in particular, the invention shown in FIG. 1 includes an oscillator 10 which outputs a continuous signal of frequency f to a gated amplifier 2 which sends amplified pulses through a transmit-receive (TR) switch 3 to a transducer 1 coupled to the test material. Echoes from reflectors within the test material are detected by the transducer 1, and sent via the TR switch 3 to a receiver amplifier 4. The amplified echoes are then sent to each of two phase detectors 5 and 6. In-phase and quadrature reference signals at frequency f are derived from a phase splitter 7 and each are sent to one of the two phase detectors 5 and 6. The outputs of the phase detectors are used, with additional amplification, to deflect the beam of a cathode ray tube 8 in orthogonal directions.

As the transducer 1 is moved over the test material with no reflectors (e.g. no flaws or boundaries), a random pattern is displayed on CRT 8. However, when the transducer passes over a reflector, a spiral pattern is displayed. The rotation about the center of the display represents phase variations and the distance of the spiral from the center of the screen indicates echo amplitude.

Figure 2:
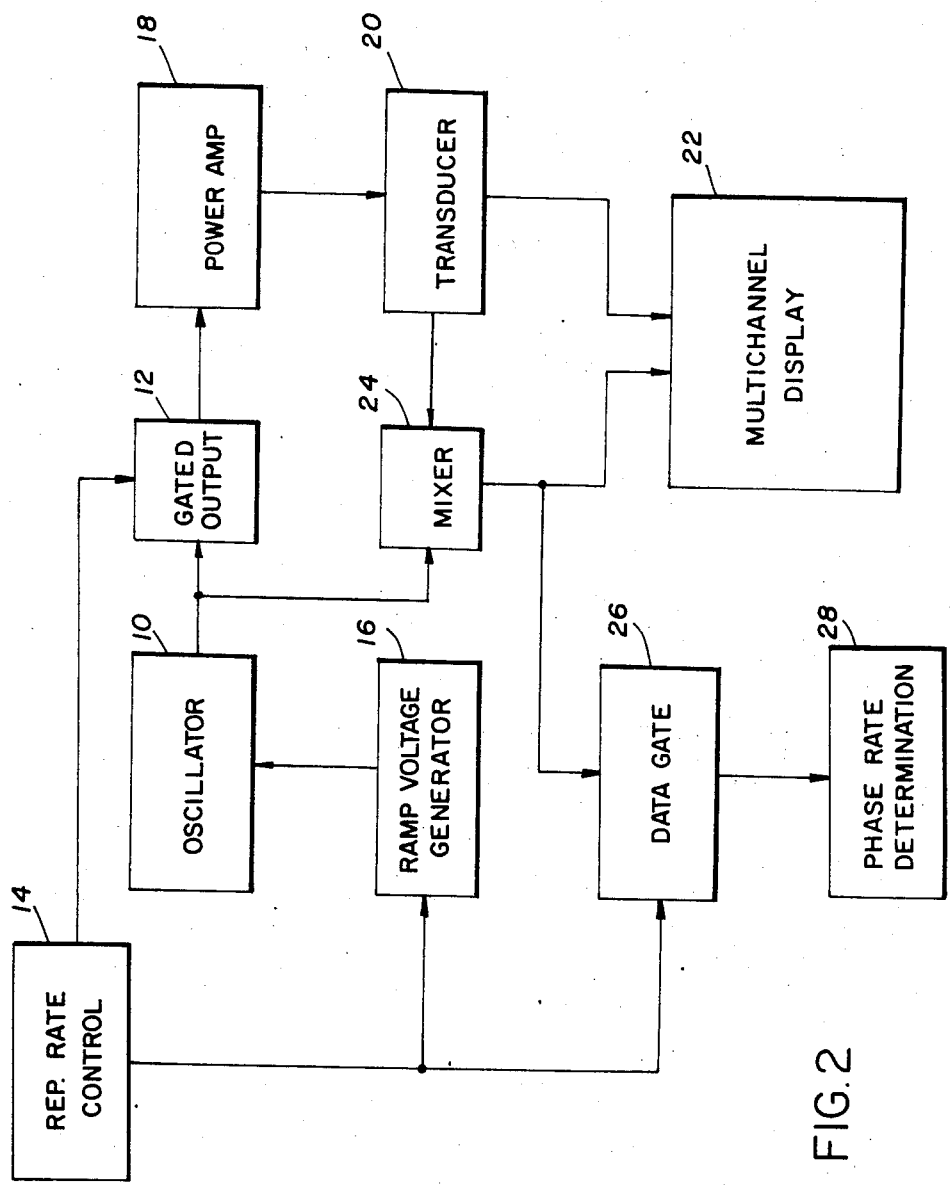
FIG. 2 is a block diagram for a second type of phase sensitive ultrasonic instrument according to the invention.

FIG. 2 shows an alternative instrument which is useful for determining defect position. A repetition rate control 14 initiates the operation of a ramp voltage generator 16 which in turn causes the oscillator 10 to sweep through a range of frequencies. The repetition rate control 14 also activates a gate 12 to allow a burst from the oscillator 10 to reach a power amplifier 18 and then to a transducer 20. A pulse of ultrasound is sent into the test material and echoes from the material returned to the transducer. These echoes are sent to a mixer 24 which also receives a reference signal from the oscillator 10. The output of the mixer is dependent upon the relative phase of the echo compared to the oscillator signal. This phase dependent signal is displayed at multichannel display 22 as a function of ramp voltage. The mixer output is also sent to a data gate 26 controlled by the repetition rate control 14, which outputs its signal to a phase rate determination circuit 28.

The embodiment of FIG. 2 can thus be utilized to determine the depth of a flaw in the material, based on the sweeping of frequency f and the use of the equation set forth above for calculating the depth R for the flaw.

While specific embodiments of the invention have been shown and described in detail to illustrate the application of the principles of the invention, it will be understood that the invention may be embodied otherwise without departing from such principles.

What is claimed is:

1. An ultrasonic apparatus for testing a material, comprising:

an oscillator for generating an oscillator signal at a selected frequency in the ultrasonic range;

transducer-receiver means connected to said oscillator for transmitting an ultrasonic signal at the selected frequency into the material from saids transducer-receiver means and for receiving an echo signal back from the material at that same transducer-receiver means;

phase detector means connected to said transducer means and to said oscillator for mixing the echo signal with an in-phase oscillator signal to produce a first display signal, and with a quadrature oscillator signal to produce a second display signal; and display means connected to said phase detector means for generating an image having a configuration which is dependent upon said first and second display signals and which varies according to the presence and depth of a reflecting structure in the material which produces said echo signal.

2. An apparatus according to claim 1, wherein said display means comprises a cathode ray tube for generating an image using orthogonal signals, said first and second display signals being utilized as said orthogonal signals.

3. An apparatus according to claim 2, wherein said phase detector means comprises a phase splitter connected to said oscillator for producing an in-phase signal and a 90° out of phase signal, a first phase detector connected to said phase splitter for receiving said in-phase signal and a second phase detector connected to said phase splitter for receiving said 90° out of phase signal, said first and second detectors generating said first and second display signals respectively, and being connected to said cathode ray tube.

4. An apparatus according to claim 3, including a gated amplifier connected to said oscillator for receiving and amplifying said oscillator signal, a transmit-receive switch connected to said gated amplifier and to said transducer for alternately supplying oscillator signals to said transducer and for receiving echo signals back from said transducer, and a receiver amplifier connected to said switch for receiving and amplifying the echo signals, said receiver amplifier being connected to said first and second phase detectors for supplying the amplified echo signal to said first and second phase detectors.

5. An apparatus according to claim 4, including frequency sweep means connected to said oscillator for sweeping said selected frequency of said oscillator signal over a selected range of frequencies, whereby said first and second display signals vary with frequency and the configuration of said image generated by said display means varies with frequency, the variations of said configuration being useable to determine a depth of a structure in said material which generates said echo signal.

6. An apparatus according to claim 5, wherein said frequency sweep means comprises a repetition rate control for repeating cycles for sweeping the selected frequency, a ramp voltage generator connected to said rate control for ramping a voltage according to the frequency sweep, said ramp voltage generator being connected to said oscillator for sweeping the selected frequency of said oscillator, a gated output unit connected to said oscillator for receiving said oscillator signals and for generating ultrasonic pulses, said gated output unit being connected to said transducer (via power amp) for causing said transducer to transmit ultrasonic pulses into the material and to receive echo signal pulses back from the material.

7. An apparatus according to claim 6, wherein said phase detector means comprises a mixer connected to said oscillator for receiving said oscillator signals and connected to said transducer for receiving said echo signals, said mixer forming one of said first and second display signals, said transducer being connected directly to said display means for producing the other of said first and second display signals which correspond to said echo signal.

8. A method of ultrasonically testing a material comprising:

generating an oscillator signal at a selected frequency in the ultrasonic range;

transmitting the oscillator signal at the selected frequency in the ultrasonic range into the material at a specific spot to form an echo signal back from the material when the oscillator signal strikes a discontinuity in the material;

receiving the echo signal back from the material at the same specific spot;

generating a first display signal by mixing the echo signal with the oscillator signal;

generating a second display signal by mixing the echo signal with a quadrature signal formed by shifting the oscillator signal by 90; and using the first and second display signals to generate a visual image whose configuration depends on a phase shift between the oscillator signal and the echo signal which in turn depends on the presence and depth of a discontinuity in the material.

9. A method according to claim 8, including sweeping the oscillator signal across a range of selected frequencies to vary the first and second display signals which in turn varies the configuration of the image, the sweep and frequency being useable to calculate a depth of the discontinuity in the material which forms the echo signal.

10. A method according to claim 8, including moving the point of entry of the oscillator signal into the material across a surface of the material to vary the echo signal from a fixed discontinuity in the material.

11. An ultrasonic apparatus for testing a material, comprising:

an oscillator for generating an oscillator signal at a selected frequency in the ultrasonic range;

transducer means connected to said oscillator for transmitting an ultrasonic signal at the selected frequency into the material and for receiving an echo signal back from the material;

phase detector means connected to said transducer means and to said oscillator for mixing the echo signal with an in-phase oscillator signal to produce a first display signal, and with a quadrature oscillator signal to produce a second display signal;

display means connected to said phase detector means for generating an image having a configuration which is dependent upon said first and second display signals and which varies according to the presence and depth of a reflecting structure in the material which produces said echo signal, said display means comprises a cathode ray tube for generating an image using orthogonal signals, said first and second display signals being utilized as said orthogonal signals;

said phase detector means including a phase splitter conector to said oscillator for producing an in-phase signal and a 90 out of phase signal, a first phase detector connected to said phase for receiving said in-phase signal and a second phase detector connected to said phase splitter for receiving said 90 out of phase signal, said first and second detectors geneating said first and second display signlas respectively, and being connected to said cathode ray tube; and a gated amplifier connected to said oscillator for receiving and amplifying said oscillator signal, a transmit-receive switch connected to said gated amplifier and to said transducer for alternately supplying oscillator signals to said transducer and for receiving echo signals back from said transducer, and a receiver amplifer connected to said switch for receiving and amplifying the echo signals, said receiver amplifier being connected to said first and second phase detectors for supplying the amplified echo signal to said first and second phase detectors.

12. An ultrasonic apparatus for testing a material, comprising;

an oscillator for generating an oscillator signal at a selected frequency in the ultrasonic range;

transducer means connected to said oscillator for transmitting an ultrasonic signal at the selected frequency into the material and for receiving an echo signal back from the material;

phase detector means connected to said transducer means and to said oscillator for mixing the echo signal with an in-phase oscillator signal to produce a first display signal, and with a quadrature oscillator signal to produce a second display signal;

display means connected to said phase detector means for generating an image having a configuration which is dependent upon said first and second display signals and which varies according to the presence and depth of a reflecting structure in the material which produces said echo signal; and frequency sweep means connected to said oscillator for sweeping said selected frequency of said oscillator signal over a selected range of frequencies, whereby said first and second display signals vary with frequency and the configuration of said image generated by said display means varies with frequency, the variations of said configurations being useable to determine a depth of a structure in said material which generates said echo signal with said frequency sweep means including a repetition rate control for repeating cycles for sweeping the selected frequency, a ramp voltage generator connected to said rate control for ramping a voltage according to the frequency sweep, said ramp voltage generator being connected to said oscillator, a gated output unit connected to said osillator for receiving said oscillator signals and for generating ultrasonic pulses, said gated output unit being connected to said transducer for causing said transducer to transmit ultrasonic pulses into the material and to receive echo signal pulses back from the material.

13. An apparatus according to claim 12, wherein said phase detector means comprises a mixer connected to said oscillator for receiving said oscillator signals and connected to said transducer for receiving said echo signals, said mixer forming one of said first and second display signals, said transducer being connected directly to said display means for producing the other of said first and second display signals which correspond to said echo signal.

* * * * *

UNITED STATES PATENT AND TRADEMARK OFFICE
CERTIFICATE OF CORRECTION

PATENT NO. : 4,702,112
DATED : Oct. 27, 1987
INVENTOR(S) : Lawrie, et al.

It is certified that error appears in the above-identified patent and that said Letters Patent are hereby corrected as shown below:

TITLE CHANGE TO:

ULTRASONIC PHASE APPARATUS

Signed and Sealed this

Eighteenth Day of October, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,702,112

DATED : Oct. 27, 1987

INVENTOR(S) : Lawrie et al.

It is certified that error appears in the above-identified patent and that said Letters Patent is hereby corrected as shown below:

In Col. 6, line 64, kindly delete "conector" and insert therefor --connector--.

In Col. 8, line 17, immediately following "oscillator" insert --for sweeping the selected frequency of said oscillator--.

In Col. 8, line 18, kindly delete "osillator" and insert therefor --oscillator--.

Signed and Sealed this

Eleventh Day of September, 1990

Attest:

HARRY F. MANBECK, JR.

*Attesting Officer*        *Commissioner of Patents and Trademarks*